United States Patent [19]
Arendt et al.

[11] Patent Number: 6,093,682
[45] Date of Patent: Jul. 25, 2000

[54] SOLID AGRICULTURAL COMPOSITION COMPRISING A MONOSACCHARIDE, AN OLIGOSACCHARIDE AND/OR A POLYSACCHARIDE

[75] Inventors: Volker Dietrich Arendt, Princeton, N.J.; Sandra Christine Miller, Morrisville, Pa.

[73] Assignee: American Cyanamid Company, Madison, N.J.

[21] Appl. No.: 09/272,915

[22] Filed: Mar. 19, 1999

Related U.S. Application Data

[60] Provisional application No. 60/079,637, Mar. 27, 1998.
[51] Int. Cl.⁷ .......................... A01N 63/00; A01N 43/40; A01N 43/64; A01N 43/84; A01N 43/68
[52] U.S. Cl. .......................... 504/118; 504/130; 504/134; 504/148; 504/226; 504/232; 504/326
[58] Field of Search ...................................... 504/116, 130, 504/134, 148, 226, 232, 326, 118

[56] References Cited

U.S. PATENT DOCUMENTS

| | | | |
|---|---|---|---|
| 5,200,401 | 4/1993 | Röchling et al. | 514/63 |
| 5,476,835 | 12/1995 | Johnson et al. | 504/247 |
| 5,656,281 | 8/1997 | Hytte et al. | 424/408 |

*Primary Examiner*—Jose' G. Dees
*Assistant Examiner*—Alton Pryor
*Attorney, Agent, or Firm*—John W. Hogan, Jr.

[57] ABSTRACT

The present invention provides solid agricultural compositions which produce stable dispersions in the presence of polyacrylamide drift control agents.

The present invention also provides stable, aqueous dispersions which are produced from the solid compositions of this invention.

**

SOLID AGRICULTURAL COMPOSITION COMPRISING A MONOSACCHARIDE, AN OLIGOSACCHARIDE AND/OR A POLYSACCHARIDE

This application claims the benefit of provisional application Ser. No. 60/079,637 filed Mar. 27, 1998.

BACKGROUND OF THE INVENTION

Agricultural compounds are commonly formulated as solid compositions such as water-dispersible, granular compositions and wettable powder compositions. Conventional solid compositions comprise an active compound, a mineral carrier, and a wetting agent and/or a dispersing agent (See e.g., U.S. Pat. No. 5,476,835).

Solid compositions are generally dispersed in water prior to use and the resultant aqueous dispersion is applied to the desired treatment locus. To prevent damage to non-target areas caused by drift of the aqueous dispersion during application, polyacrylamide drift control agents are often added to the aqueous dispersion prior to application. However, it has been found that aqueous dispersions obtained from conventional solid compositions which contain mineral carriers are not entirely stable in the presence of polyacrylamide drift control agents. Such instability may result in the formation of a significant amount of sediment which may clog the nozzles and filters of the application equipment. Accordingly, there is a need in the art for a solid composition which forms a stable dispersion in the presence of polyacrylamide drift control agents.

SUMMARY OF THE INVENTION

The present invention provides solid compositions which form stable, aqueous dispersions in the presence of polyacrylamide drift control agents.

The solid compositions of this invention comprise one or more agricultural compounds; a monosaccharide, an oligosaccharide or a polysaccharide or a mixture thereof; and a dispersing agent.

The present invention also provides a stable, aqueous dispersion which comprises a solid composition of this invention; a polyacrylamide drift control agent; and water.

DETAILED DESCRIPTION OF THE INVENTION

The solid compositions of this invention which produce stable, aqueous dispersions preferably comprise on a weight to weight basis about 10% to 95% of one or more agricultural compounds; about 5% to 60% of a monosaccharide, an oligosaccharide or a polysaccharide or a mixture thereof; about 1% to 15% of a dispersing agent; and 0% to about 15% of a wetting agent.

More preferred solid compositions of this invention comprise on a weight to weight basis about 45% to 80% of one or more agricultural compounds; about 10% to 50% of a monosaccharide, an oligosaccharide or a polysaccharide or a mixture thereof; about 2% to 15% of a dispersing agent; and about 1% to 6% of a wetting agent.

Surprisingly, it has been found that the solid compositions of the present invention which comprise a monosaccharide, oligosaccharide and/or polysaccharide carrier form aqueous dispersions which are significantly more stable in the presence of polyacrylamide drift control agents than conventional solid compositions which comprise a mineral carrier such as kaolin clay.

Monosaccharides suitable for use in this invention include, but are not limited to, pentoses such as ribose, ribulose, arabinose, xylose, lyxose and xylulose; hexoses such as glucose, fructose, galactose, mannose and sorbose; trioses; tetroses; heptoses; and octoses. The term oligosaccharide as used in the specification and claims is defined as a carbohydrate containing 2 to 9 monosaccharides linked together. Oligosaccharides suitable for use in the compositions of this invention include, but are not limited to, disaccharides such as sucrose, maltose, lactose and trehalose. The term polysaccharide as used in the specification and claims is defined as a carbohydrate containing 10 or more monosaccharides linked together. Polysaccharides suitable for use in the present invention include, but are not limited to, starches such as corn starch, potato starch, rice starch, tapioca starch and wheat starch; modified starches such as dextrins; genetically modified starches such as corn starches comprising 100% amylopectin, or a mixture of amylopectin and amylose (such as 50% amylopectin and 50% amylose or 30% amylopectin and 70% amylose); glycogen; agar; pectin; carrageenan; and natural gums such as arabic gum, guar gum, karaya gum and tragacanth gum; and mixtures thereof.

Surprisingly, it has been found that compositions of this invention which comprise a starch/dextrin mixture as carrier provide aqueous dispersions which are especially stable in the presence of a polyacrylamide drift control agent. In particular, it has been found that compositions of this invention which comprise a starch to dextrin ratio of about 20:1 to 1:1, preferably about 5:1 to 3:1 and more preferably about 4:1, provide aqueous dispersions which are highly stable in the presence of polyacrylamide drift control agents.

Agricultural compounds suitable for use in this invention include, but are not limited to, herbicides, insecticides, acaricides, fungicides, molluscicides, nematicides, plant growth regulators, safeners, algicides, mildewicides and the like or combinations thereof. Preferably, the melting point of the agricultural compound(s) is/are above about 50° C., more preferably above about 60° C. and most preferably above about 65° C. to ensure that the solid composition remains physically stable in hot climates. Herbicides, insecticides, acaricides, fungicides and molluscicides are preferred agricultural compounds for use in the solid composition of this invention.

Herbicides suitable for use in the solid compositions of this invention include, but are not limited to, imidazolinone herbicides such as imazamethabenz-methyl, imazamox, imazapic, imazapyr, imazaquin, and imazethapyr;

1,3,5-triazine herbicides such as ametryn, atrazine, cyanazine, desmetryn, dimethametryn, prometon, prometryn, propazine, simazine, simetryn, terbumeton, terbuthylazine, terbutryn, and trietazine;

1,2,4-triazinone herbicides such as hexazinone, metamitron, and metribuzin;

sulfonylurea herbicides such as amidosulfuron, azimsulfuron, bensulfuron-methyl, chlorimuron-ethyl, chlorsulfuron, cinosulfuron, ethametsulfuron-methyl, ethoxysulfuron, flazasulfuron, flupyrsulfuron-methyl-sodium, halosulfuron-methyl, imazosulfuron, metsulfuron-methyl, nicosulfuron, oxasulfuron, primisulfuron-methyl, prosulfuron, pyrazosulfuron-ethyl, rimsulfuron, sulfometuron-methyl, sulfosulfuron, thifensulfuron-methyl, triasulfuron, tribenuron-methyl, and triflusulfuron-methyl;

2,6-dinitroaniline herbicides such as benfluralin, butralin, dinitramine, ethalfluralin, fluazinam, fluchloralin, flumetralin, oryzalin, pendimethalin, prodiamine, and trifluralin;

urea herbicides such as chlorbromuron, chlorortoluron, dimefuron, diuron, fenuron, fluometuron, isoproturon, isouron, linuron, methabenzthiazuron, metobenzuron, metobromuron, metoxuron, monolinuron, neburon, siduron, and tebuthiuron;
pyridazinone herbicides such as norflurazon and chloridazon;
quinolinecarboxylic acid herbicides such as quinclorac and quinmerac;
uracil herbicides such as bromacil, lenacil, and terbacil;
triazolopyrimidine sulfonanilide herbicides such as cloransulam-methyl, flumetsulam, and metosulam;
sulfamoylurea herbicides such as cyclosulfamuron;
sulfentrazone;
glyphosate; glyphosate-ammonium; glyphosate-sodium; glyphosate-trimesium;
and isoxaflutole.

Insecticides suitable for use in the solid compositions of this invention include, but are not limited to,
pyrrole insecticides such as chlorfenapyr;
pyrethroid insecticides such as acrinathrin, allethrin [(1R)-isomers], bifenthrin, bioallethrin, bioallethrin S-cyclopentenyl isomer, bioresmethrin, cycloprothrin, byfluthrin, beta-cyfluthrin, cyhalothrin, lambda-cyhalothrin, cypermethrin, alpha-cypermethrin, beta-cypermethrin, theta-cypermethrin, zeta-cypermethrin, cyphenothrin [(1R)-trans-isomers], deltamethrin, empenthrin [(EZ)-(1R)-isomers], esfenvalerate, fenpropathrin, fenvalerate, flucythrinate, flumethrin, tau-fluvalinate, imiprothrin, permethrin, phenothrin [(1R)-trans-isomer], prallethrin, resmethrin, tefluthrin, tetramethrin, tetramethrin [(1R)-isomers], tralomethrin, and transfluthrin;
non-ester pyrethroid insecticides such as etofenprox, flufenprox, halfenprox, and silafluofen;
benzoylurea insecticides such as chlorfluazuron, diflubenzuron, fluazuron, flucycloxuron, flufenoxuron, hexaflumuron, lufenuron, novaluron, teflubenzuron, and triflumuron;
organophosphorus insecticides such as acephate, azinphos-methyl diazinon, methidathion, phorate, phosmet, terbufos, and the like;
carbamate insecticides such as carbaryl, carbofuran, and the like;
cyclodiene organochlorine insecticides such as chlordane, endosulfan, and heptachlor;
oxime carbamate insecticides such as alanycarb, aldicarb, butocarboxim, butoxycarboxim, methomyl, oxamyl, thiodicarb, and thiofanox;
diacylhydrazine insecticides such as halofenozide and tebufenozide;
cyromazine; and
biological insecticides such as *Bacillus thuringiensis*.

Fungicides suitable for use in the solid compositions of this invention include, but are not limited to,
morpholine fungicides such as dimethomorph, dodemorph, fenpropimorph, and tridemorph;
azole fungicides such as azaconazole, bitertanol, bromuconazole, cyproconazole, difenoconazole, diniconazole, fenbuconazole, fluquinconazole, flusilazole, flutriafol, hexaconazole, imazalil, imibenconazole, ipconazole, metconazole, myclobutanil, paclobutrazol, pefurazoate, penconazole, prochloraz, propiconazole, tebuconazole, tetraconazole, triadimefon, triadimenol, triflumizole, triticonazole, and uniconazole;
carboxamide fungicides such as carboxin, fenfuram, flutolanil, mepronil, and oxycarboxin;
dicarboximide fungicides such as chlozolinate, iprodione, procymidone, and vinclozolin;
pyrimidinyl carbinol fungicides such as ancymidol, flurprimidol, nuarimol, and fenarimol;
N-trihalomethylthio fungicides such as captafol, captan, dichlorfluanid, folpet, and tolylfluanid;
alkylenebis(dithiocarbamate) fungicides such as mancopper, mancozeb, maneb, metiram, nabam, propineb, and zineb;
benzimidazole fungicides such as benomyl, carbendazim, debacarb, fuberidazole, and thiabendazole; and
chlorothalonil.

Herbicidal compounds especially suitable for use in the present invention include imidazolinone compounds such as imazapyr, imazaquin, imazethapyr, imazapic and imazamox, urea compounds such as diuron, and 1,3,5-triazine compounds such as atrazine, and mixtures thereof with a mixture of imazapyr and diuron being especially preferred. Insecticidal compounds especially suitable for use in the present invention include pyrrole compounds such as chlorfenapyr. Fungicidal compounds especially suitable for use in the compositions of this invention include morpholine compounds such as dimethomorph.

Dispersing agents useful in the solid compositions of this invention include any of the conventional dispersing agents which are well known in the art. In particular, anionic dispersing agents such as sodium lignosulfonate, sodium naphthalene formaldehyde condensate and the like and mixtures thereof are preferred. Sodium naphthalene formaldehyde condensate is especially preferred.

Wetting agents suitable for use in the solid compositions of this invention include any of the conventional wetting agents which are well known in the art. In particular, anionic wetting agents such as sodium N-methyl-N-oleyoyltaurate, octylphenoxy polyethoxy ethanol, nonylphenoxy polyethoxy ethanol, sodium dioctyl sulfosuccinate, sodium dodecyl benzyl sulfonate, sodium lauryl sulfonate, sodium alkyl naphthalene sulfonate, sodium sulfonated alkyl carboxylate and the like and mixtures thereof are preferred. An especially preferred wetting agent for use in the compositions of the present invention is a mixture of sodium alkyl naphthalene sulfonate and sodium sulfonated alkyl carboxylate.

The solid compositions of this invention may also contain additional ingredients conventionally used in the solid formulations art including, but not limited to, anti-foaming agents, dyes, binders and the like. In particular, the compositions of this invention may contain up to about 1% by weight of an anti-foaming agent.

Another more preferred solid composition of this invention comprises on a weight to weight basis about 45% to 80% of one or more agricultural compounds selected from the group consisting of a herbicide, an insecticide and a fungicide; about 10% to 50% of a mixture of starch and dextrin; about 2% to 15% sodium naphthalene formaldehyde condensate; about 1% to 6% of a mixture of sodium alkyl naphthalene sulfonate and sodium sulfonated alkyl carboxylate; and up to about 1% of an anti-foaming agent.

A most preferred solid composition of this invention comprises on a weight to weight basis about 6% to 10% imazapyr; about 60% to 67% diuron; about 12% to 16% of a mixture of starch and dextrin having a ratio of starch to dextrin of about 5:1 to 3:1; about 7% to 11% sodium naphthalene formaldehyde condensate; about 2% to 4% of a mixture of sodium alkyl naphthalene sulfonate and sodium sulfonated alkyl carboxylate; and up to about 1% of an anti-foaming agent.

The solid compositions of this invention may be prepared as wettable powder compositions, granular compositions, and the like. Preferably, the solid compositions of this invention are granular compositions.

Wettable powder compositions of this invention may be prepared by conventional methods such as blending the ingredients together and milling the blend to obtain a powder. Granular compositions of this invention may be prepared by conventional procedures including, but not limited to, pan-granulation, compaction and extrusion.

Preferably, the granular compositions of the present invention may be prepared, in general, by admixing one or more agricultural compounds; the monosaccharide, oligosaccharide or polysaccharide or mixture thereof; the dispersing agent; and optionally the wetting agent and/or additional ingredients to obtain a homogeneous mixture. The homogeneous mixture is wetted with about 5% to 15% wt/wt water, and blended to obtain an extrudable material. The extrudable material is then passed through a conventional extruder such as a basket extruder, dried and screened to obtain the granular compositions of this invention.

The solid compositions of this invention are dispersed in water prior to use and the resultant aqueous dispersion is applied to the desired treatment locus. Advantageously, it has been found that stable, aqueous dispersions are obtained when a polyacrylamide drift control agent is added to aqueous dispersions of the solid compositions of this invention. Accordingly, the present invention further relates to a stable, aqueous dispersion which comprises a solid composition of this invention; a polyacrylamide drift control agent; and water.

Amounts of the components of suitable aqueous dispersions of the present invention can vary based upon the use rate and concentration of the particular agricultural compound or composition, the necessary or desirable level of drift control, and environmental conditions such as wind. Preferred aqueous dispersions of this invention comprise on a weight to weight basis about 0.001% to 20% of the solid composition of the present invention; about 0.001% to 1% (preferably 0.008% to 0.5%) of a polyacrylamide drift control agent; and water.

The present invention also provides a method for the preparation of the stable, aqueous dispersions of this invention which method comprises: (a) dispersing a solid composition of the present invention in water to obtain a dispersion; and (b) adding a polyacrylamide drift control agent to the dispersion obtained in (a).

This invention also provides a method for controlling pests such as weeds, insects, acarina, fungi, nematodes and the like by applying to the locus of the pest a pesticidally effective amount of a solid composition or an aqueous dispersion of the present invention. In particular, this invention provides a method for controlling undesirable plant species which comprises applying to the foliage of the plants or to the soil or water containing seeds or other propagating organs thereof, a herbicidally effective amount of a herbicidal aqueous dispersion which comprises a solid composition of this invention containing one or more herbicides; a polyacrylamide drift control agent; and water.

In order to facilitate a further understanding of this invention, the following examples are presented primarily for the purpose of illustrating more specific details thereof. The invention should not be deemed limited thereby except as defined in the claims.

EXAMPLE 1
Preparation of Granular Compositions

A mixture of imazapyr (183.70 g, 97% technical material), diuron (1,469.45 g, 97% technical material), PURE-DENT® B700 corn starch (269.60 g, commercially available from Grain Processing Corporation, Muscatine, Iowa), C-Star Plus 08505 dextrin (67.40 g, commercially available from Cerestar USA, Inc., Hammond, Ind.), MORWET® D-425 (204.10 g, a sodium naphthalene formaldehyde condensate commercially available from Witco Inc., Houston, Tex.), MORWET® EFW (68.05 g, a proprietary blend of sodium alkyl naphthalene sulfonate and sodium sulfonated alkyl carboxylate commercially available from Witco Inc.), and FOAMASTER® Soap L sodium tallowate (5.65 g, commercially available from Henkel Corporation, Cincinnati, Ohio) is blended to obtain a homogeneous mixture. The homogeneous mixture is wetted with 6% to 8% wt/wt water, and blended for 5 minutes to obtain an extrudable material. This material is extruded using a basket extruder. The extruded material is dried and screened to obtain the granular composition identified as composition number 1 in Table I.

Using essentially the same procedure, the granular compositions identified as composition numbers 2–52 in Table I may be prepared.

TABLE I

Granular Compositions

Ingredient/wt/wt %

| Composition Number | Agricultural Compound | Oligosaccharide or Polysaccharide | MORWET ® D-425 | MORWET ® EFW | FOAMASTER ® Soap L |
|---|---|---|---|---|---|
| 1 | Imazapyr/8.10 Diuron/64.79 | Starch[1]/11.89 Dextrin[2]/2.97 | 9.00 | 3.00 | 0.25 |
| 2 | Imazapyr/7.90 Diuron/63.86 | Sucrose/18.99 | 6.00 | 3.00 | 0.25 |
| 3 | Imazapyr/7.90 Diuron/63.86 | Starch[1]/18.99 | 6.00 | 3.00 | 0.25 |
| 4 | Imazapyr/7.90 Diuron/63.86 | Starch[3]/18.99 | 6.00 | 3.00 | 0.25 |
| 5 | Imazapyr/7.90 Diuran/63.86 | Starch[4]/18.99 | 6.00 | 3.00 | 0.25 |
| 6 | Imazapyr/7.90 Diuron/63.86 | Dextrin[2]/18.99 | 6.00 | 3.00 | 0.25 |
| 7 | Imazapyr/7.90 Diuron/63.86 | Starch[5]/18.99 | 6.00 | 3.00 | 0.25 |
| 8 | Imazapyr/7.90 Diuron/63.86 | Starch[1]/10.99 Dextrin[2]/8.00 | 6.00 | 3.00 | 0.25 |

TABLE I-continued

Granular Compositions

Ingredient/wt/wt %

| Composition Number | Agricultural Compound | Oligosaccharide or Polysaccharide | MORWET ® D-425 | MORWET ® EFW | FOAMASTER ® Soap L |
|---|---|---|---|---|---|
| 9 | Imazapyr/7.90 Diuron/63.86 | Starch[1]/13.29 Dextrin[2]/5.70 | 6.00 | 3.00 | 0.25 |
| 10 | Imazapyr/7.90 Diuron/63.86 | Starch[1]/15.19 Dextrin[2]/3.80 | 6.00 | 3.00 | 0.25 |
| 11 | Imazapyr/7.90 Diuron/63.86 | Starch[1]/17.09 Dextrin[2]/1.90 | 6.00 | 3.00 | 0.25 |
| 12 | Imazapyr/7.90 Diuron/63.86 | Starch[1]/18.04 Dextrin[2]/0.95 | 6.00 | 3.00 | 0.25 |
| 13 | Imazapyr/7.90 Diuron/63.86 | Starch[1]/7.99 Dextrin[2]/8.00 | 9.00 | 3.00 | 0.25 |
| 14 | Imazapyr/7.90 Diuron/63.86 | Starch[1]/9.99 Dextrin[2]/6.00 | 9.00 | 3.00 | 0.25 |
| 15 | Imazapyr/7.90 Diuron/63.86 | Starch[1]/13.99 Dextrin[2]/2.00 | 9.00 | 3.00 | 0.25 |
| 16 | Imazapyr/7.90 Diuron/63.86 | Starch[1]/25.99 | 2.00 | — | 0.25 |
| 17 | Imazapyr/7.90 Diuron/63.86 | Starch[1]/23.99 | 2.00 | 2.00 | 0.25 |
| 18 | Imazapyr/7.90 Diuron/63.86 | Starch[1]/19.99 | 2.00 | 6.00 | 0.25 |
| 19 | Imazapyr/7.90 Diuron/63.86 | Starch[1]/15.99 | 2.00 | 10.00 | 0.25 |
| 20 | Imazapyr/7.90 Diuron/63.86 | Starch[1]/21.99 | 6.00 | — | 0.25 |
| 21 | Imazapyr/7.90 Diuron/63.86 | Starch[1]/19.99 | 6.00 | 2.00 | 0.25 |
| 22 | Imazapyr/7.90 Diuron/63.86 | Starch[1]/15.99 | 6.00 | 6.00 | 0.25 |
| 23 | Imazapyr/7.90 Diuron/63.86 | Starch[1]/11.99 | 6.00 | 10.00 | 0.25 |
| 24 | Imazapyr/7.90 Diuron/63.86 | Starch[1]/17.99 | 10.00 | — | 0.25 |
| 25 | Imazapyr/7.90 Diuron/63.86 | Starch[1]/15.99 | 10.00 | 2.00 | 0.25 |
| 26 | Imazapyr/7.90 Diuron/63.86 | Starch[1]/11.99 | 10.00 | 6.00 | 0.25 |
| 27 | Imazapyr/7.90 Diuron/63.86 | Starch[1]/7.99 | 10.00 | 10.00 | 0.25 |
| 28 | Imazapyr/7.90 Diuron/63.86 | Starch[1]/13.00 Dextrin[2]/12.99 | 2.00 | — | 0.25 |
| 29 | Imazapyr/7.90 Diuron/63.86 | Starch[1]/12.00 Dextrin[2]/11.99 | 2.00 | 2.00 | 0.25 |
| 30 | Imazapyr/7.90 Diuron/63.86 | Starch[1]/10.00 Dextrin[2]/9.99 | 2.00 | 6.00 | 0.25 |
| 31 | Imazapyr/7.90 Diuron/63.86 | Starch[1]/8.00 Dextrin[2]/7.99 | 2.00 | 10.00 | 0.25 |
| 32 | Imazapyr/7.90 Diuron/63.86 | Starch[1]/11.00 Dextrin[2]/10.99 | 6.00 | — | 0.25 |
| 33 | Imazapyr/7.90 Diuron/63.86 | Starch[1]/10.00 Dextrin[2]/9.99 | 6.00 | 2.00 | 0.25 |
| 34 | Imazapyr/7.90 Diuron/63.86 | Starch[1]/9.50 Dextrin[2]/9.49 | 6.00 | 3.00 | 0.25 |
| 35 | Imazapyr/7.90 Diuron/63.86 | Starch[1]/8.00 Dextrin[2]/7.99 | 6.00 | 6.00 | 0.25 |
| 36 | Imazapyr/7.90 Diuron/63.86 | Starch[1]/6.00 Dextrin[2]/5.99 | 6.00 | 10.00 | 0.25 |
| 37 | Imazapyr/7.90 Diuron/63.86 | Starch[1]/9.00 Dextrin[2]/8.99 | 10.00 | — | 0.25 |
| 38 | Imazapyr/7.90 Diuron/63.86 | Starch[1]/8.00 Dextrin[2]/7.99 | 10.00 | 2.00 | 0.25 |
| 39 | Imazapyr/7.90 Diuron/63.86 | Starch[1]/6.00 Dextrin[2]/5.99 | 10.00 | 6.00 | 0.25 |
| 40 | Imazapyr/7.90 Diuron/63.86 | Starch[1]/4.00 Dextrin[2]/3.99 | 10.00 | 10.00 | 0.25 |
| 41 | Imazapyr/7.90 Diuron/63.86 | Starch[1]/8.99 Dextrin[2]/9.00 | 8.00 | 2.00 | 0.25 |
| 42 | Imazaquin/74.88 | Starch[1]/14.50 Dextrin[2]/3.62 | 4.50 | 2.50 | — |
| 43 | Atrazine/74.72 | Starch[1]/16.22 Dextrin[2]/4.06 | 3.00 | 2.00 | — |

TABLE I-continued

Granular Compositions

Ingredient/wt/wt %

| Composition Number | Agricultural Compound | Oligosaccharide or Polysaccharide | MORWET ® D-425 | MORWET ® EFW | FOAMASTER ® Soap L |
|---|---|---|---|---|---|
| 44 | Chlorfenapyr/50.00 | Starch[1]/35.20 Dextrin[2]/8.80 | 4.00 | 2.00 | — |
| 45 | Dimethomorph/50.00 | Starch[1]/35.20 Dextrin[2]/8.80 | 4.00 | 2.00 | — |
| 46 | Imazaquin/18.04 Glyphosate/54.12 | Starch[1]/12.47 Dextrin[2]/3.12 | 9.0 | 3.0 | 0.25 |
| 47 | Imazethapyr/18.04 Glyphosate/54.12 | Starch[1]/12.47 Dextrin[2]/3.12 | 9.0 | 3.0 | 0.25 |
| 48 | Chlorimuron-ethyl/72.16 | Starch[1]/12.47 Dextrin[2]/3.12 | 9.0 | 3.0 | 0.25 |
| 49 | Diflubenzuron/72.16 | Starch[1]/12.47 Dextrin[2]/3.12 | 9.0 | 3.0 | 0.25 |
| 50 | Acephate/72.16 | Starch[1]/12.47 Dextrin[2]/3.12 | 9.0 | 3.0 | 0.25 |
| 51 | Chlorothalonil/72.16 | Starch[1]/12.47 Dextrin[2]/3.12 | 9.0 | 3.0 | 0.25 |
| 52 | Tebuconazole/72.16 | Starch[1]/12.47 Dextrin[2]/3.12 | 9.0 | 3.0 | 0.25 |

[1]PURE-DENT ® B700 corn starch, commercially available from Grain Processing Corporation, Musatine, Iowa.
[2]C-STAR PLUS 08505 dextrin, commercially available from Cerestar USA, Inc., Hammond, Indiana.
[3]C-STAR DryGel corn starch, commercially available from Cerestar USA, Inc.
[4]Clinton 106 B corn starch, commercially available from Clinton Corn Starch Company, Clinton, Iowa.
[5]Amylomaize VII genetically modified corn starch containing 70% amylose and 30% amylopectin, commercially available from Cerestar USA, Inc.

EXAMPLE 2

Evaluation of the stability of dispersions containing the granular compositions of this invention and a polyacrylamide drift control agent This test evaluates the stability of dispersions obtained from the granular compositions of this invention in the presence of polyacrylamide drift control agents. The test is conducted by dispersing from 0.107 g to 5.8 g of the test composition in 100 ml of water in a stoppered 100 ml graduated cylinder, inverting the cylinder 30 times, adding NALCO-TROL® II (a polyacrylamide spray adjuvant commercially available from Nalco Chemical Company, Chicago, Ill.) at a rate of 0.0075 g or 0.482 g per 100 ml of dispersion, inverting the resultant polyacrylamide containing dispersion 30 times, and evaluating the stability of the dispersion after 5 or 30 minutes. The results are reported in Table II according to the composition number from Table I. Comparative kaolin compositions are reported by letter and identified below in Table III. The comparative kaolin compositions are prepared using essentially the same procedure described in Example 1 except that kaolin clay is used in place of the monosaccharide, oligosaccharide or polysaccharide.

As can be seen from the data in Table II, dispersions prepared from the granular compositions of this invention are significantly more stable in the presence of polyacrylamide drift control agents than dispersions prepared from conventional granular compositions which contain kaolin clay.

TABLE II

| Composition Number | Agricultural Compound | Rate of NALCO-TROL ® II (g/100 ml) | Stability | Holding Period (minutes) |
|---|---|---|---|---|
| 1 | Imazapyr/Diuron[1] | 0.0075 | Stable | 5 |
| 2 | Imazapyr/Diuron | 0.0075 | Stable | 5 |
| 3 | Imazapyr/Diuron | 0.0075 | Stable | 5 |
| 4 | Imazapyr/Diuron | 0.0075 | Stable | 5 |
| 5 | Imazapyr/Diuron | 0.0075 | Stable | 5 |
| 6 | Imazapyr/Diuron | 0.0075 | Stable | 5 |
| 7 | Imazapyr/Diuron | 0.0075 | Stable | 5 |
| 41 | Imazapyr/Diuron | 0.0075 | Stable | 5 |
| Kaolin Composition A | Imazapyr/Diuron | 0.0075 | Settles | 5 |
| 1 | Imazapyr/Diuron | 0.482 | 7 ml Sediment | 30 |
| 9 | Imazapyr/Diuron | 0.482 | 8 ml Sediment | 30 |
| Kaolin Composition A | Imazapyr/Diuron | 0.482 | 22 ml Sediment | 30 |
| 42 | Imazaquin[2] | 0.482 | Trace Sediment | 30 |
| Kaolin Composition B | Imazaquin | 0.482 | Settles | 30 |
| 43 | Atrazine[1] | 0.482 | 1 ml Sediment | 30 |

TABLE II-continued

| Composition Number | Agricultural Compound | Rate of NALCO-TROL ® II (g/100 ml) | Stability | Holding Period (minutes) |
|---|---|---|---|---|
| Kaolin Composition C | Atrazine | 0.482 | 10 ml Sediment | 30 |
| 44 | Chlorfenapyr[4] | 0.482 | <1 ml Sediment | 30 |
| Kaolin Composition D | Chlorfenapyr | 0.482 | Settles | 30 |
| 45 | Dimethomorph[5] | 0.482 | <1 ml Sediment | 30 |
| Kaolin Composition E | Dimethomorph | 0.482 | 1 ml Sediment | 30 |

[1]All imazapyr/diuron compositions were tested at a rate of 5.8 g per 100 ml water.
[2]All imazaquin compositions were tested at a rate of 0.107 g per 100 ml water.
[3]All atrazine compositions were tested at a rate of 1.7 g per 100 ml water.
[4]All chlorfenapyr compositions were tested at a rate of 0.48 g per 100 ml water.
[5]All dimethomorph compositions were tested at a rate of 0.6 g per 100 ml water.

TABLE III

Comparative Kaolin Compositions

Ingredient/wt/wt %

| Kaolin Composition Letter | Agricultural Compound | Kaolin[1] | MORWET ® D-425 | MORWET ® EFW | FOAMASTER ® Soap L |
|---|---|---|---|---|---|
| A | Imazapyr/8.10 Diuron/64.79 | 17.86 | 6.00 | 3.00 | 0.25 |
| B | Imazaquin/74.88 | 18.12 | 4.50 | 2.50 | — |
| C | Atrazine/74.72 | 20.28 | 3.00 | 2.00 | — |
| D | Chlorfenapyr/50.00 | 44.00 | 4.00 | 2.00 | — |
| E | Dimethomorph/50.00 | 44.00 | 4.00 | 2.00 | — |

[1]Kaolin T-41 commercially available from Southern Clay Co., Aiken, South Carolina.

What is claimed is:

1. A solid composition which comprises (a) one or more agricultural compounds selected from the group consisting of a herbicide, an insecticide, an acaricide, a morpholine fungicide and a molluscicide; (b) a monosaccharide, an oligosaccharide or a polysaccharide or a mixture thereof; (c) a dispersing agent; provided the solid composition forms a stable aqueous dispersion in the presence of a polyacrylamide drift control agent and optionally (d) a wetting agent.

2. The composition according to claim 1 which comprises on a weight to weight basis about 10% to 95% of the one or more agricultural compounds; about 5% to 60% of the monosaccharide, the oligosaccharide or the polysaccharide or the mixture thereof; about 1% to 15% of the dispersing agent; and 0% to about 15% of the wetting agent.

3. The composition according to claim 2 which comprises about 45% to 80% of one or more agricultural compounds; about 10% to 50% of the monosaccharide, the oligosaccharide or the polysaccharide or the mixture thereof; about 2% to 15% of the dispersing agent; and about 1% to 6% of the wetting agent.

4. The composition according to claim 1 wherein the monosaccharide is selected from the group consisting of a pentose, a hexose, a triose, a tetraose, a heptose, an octose, and mixtures thereof; the oligosaccharide is a disaccharide or mixture of disaccharides; and the polysaccharide is selected from the group consisting of a starch, a modified starch, glycogen, agar, pectin, carrageenan, a natural gum, and mixtures thereof.

5. The composition according to claim 4 wherein the modified starch is a dextrin.

6. The composition according to claim 4 wherein the polysaccharide is a mixture of starch and dextrin.

7. The composition according to claim 6 wherein the ratio of starch to dextrin is about 20:1 to 1:1.

8. The composition according to claim 7 wherein the ratio is about 5:1 to 3:1.

9. The composition according to claim 8 wherein the ratio is about 4:1.

10. The composition according to claim 1 wherein the herbicide is selected from the group consisting of an imidazolinone compound, atrazine, diuron, and mixtures thereof; the insecticide is chlorfenapyr; and the fungicide is dimethomorph.

11. The composition according to claim 1 wherein the dispersing agent is selected from the group consisting of sodium lignosulfonate, sodium naphthalene formaldehyde condensate, and mixtures thereof.

12. The composition according to claim 11 wherein the dispersing agent is sodium naphthalene formaldehyde condensate.

13. The composition according to claim 2 wherein the wetting agent is selected from the group consisting of sodium N-methyl-N-oleyoyltaurate, octylphenoxy polyethoxy ethanol, nonylphenoxy polyethoxy ethanol, sodium dioctyl sulfosuccinate, sodium dodecyl benzyl sulfonate, sodium lauryl sulfonate, sodium alkyl naphthalene sulfonate, sodium sulfonated alkyl carboxylate, and mixtures thereof.

14. The composition according to claim 13 wherein the wetting agent is a mixture of sodium alkyl naphthalene sulfonate and sodium sulfonated alkyl carboxylate.

15. The composition according to claim 2 which further comprises up to about 1% of an anti-foaming agent.

16. The composition according to claim 2 which comprises about 45% to 80% of one or more agricultural compounds selected from the group consisting of a herbicide, an insecticide and a fungicide; about 10% to 50% of a mixture of starch and dextrin; about 2% to 15% sodium naphthalene formaldehyde condensate; about 1% to 6% of a mixture of sodium alkyl naphthalene sulfonate and sodium sulfonated alkyl carboxylate; and up to about 1% of an anti-foaming agent.

17. The composition according to claim 16 wherein the ratio of starch to dextrin is about 20:1 to 1:1.

18. The composition according to claim 17 wherein the ratio is about 5:1 to 3:1.

19. The composition according to claim 18 wherein the ratio is about 4:1.

20. The composition according to claim 16 wherein the herbicide is selected from the group consisting of an imidazolinone compound, atrazine, diuron, and mixtures thereof; the insecticide is chlorfenapyr; and the fungicide is dimethomorph.

21. The composition according to claim 16 which comprises about 6% to 10% imazapyr; about 60% to 67% diuron; about 12% to 16% of a mixture of starch and dextrin having a ratio of starch to dextrin of about 5:1 to 3:1; about 7% to 11% sodium naphthalene formaldehyde condensate; about 2% to 4% of a mixture of sodium alkyl naphthalene sulfonate and sodium sulfonated alkyl carboxylate; and up to about 1% of an anti-foaming agent.

22. An aqueous dispersion which comprises a solid composition; a polyacrylamide drift control agent; and water, wherein the solid composition comprises (a) one or more agricultural compounds; (b) a monosaccharide, an oligosaccharide or a polysaccharide or a mixture thereof; (c) a dispersing agent; and optionally (d) a wetting agent.

23. The aqueous dispersion according to claim 22 which comprises on a weight to weight basis about 0.001% to 20% of the solid composition; about 0.001% to 1.0% of the polyacrylamide drift control agent; and water.

24. A method for controlling a pest which comprises applying to the locus of the pest a pesticidally effective amount of an aqueous dispersion wherein the aqueous dispersion is as described in claim 22.

25. A method for the preparation of an aqueous dispersion comprising a solid composition; a polyacrylamide drift control agent; and water, wherein the solid composition comprises (a) one or more agricultural compounds; (b) a monosaccharide, an oligosaccharide or a polysaccharide or a mixture thereof; (c) a dispersing agent; and optionally (d) a wetting agent, which method comprises the steps of:

(a) adding the solid composition in water to obtain a dispersion; and (b) adding a polyacrylamide drift control agent to the dispersion obtained in step (a).

* * * * *